United States Patent [19]

Lantzsch et al.

[11] 4,252,820
[45] Feb. 24, 1981

[54] ARTHROPODICIDAL 2,2-DIMETHYL-3-(2-PERFLUOROALKYL-2-PERHALOALKYL-VINYL)-CYCLOPROPANECARBOXYLIC ACID ESTERS

[75] Inventors: Reinhard Lantzsch, Leverkusen; Hermann Hagemann; Ingeborg Hammann, both of Cologne; Wolfgang Behrenz, Overath; Bernhard Homeyer, Leverkusen, all of Fed. Rep. of Germany

[73] Assignee: Bayer Aktiengesellschaft, Leverkusen, Fed. Rep. of Germany

[21] Appl. No.: 53,676

[22] Filed: Jul. 2, 1979

[30] Foreign Application Priority Data

Jul. 15, 1978 [DE] Fed. Rep. of Germany ....... 2831193

[51] Int. Cl.³ ............... A01N 37/08; A01N 37/34; C07C 69/743; C07C 121/48
[52] U.S. Cl. .................. 424/304; 260/326 A; 260/347.2; 260/347.4; 260/465 D; 260/465.7; 568/303; 424/272; 424/274; 424/275; 424/285; 424/305; 548/131; 548/132; 549/60; 549/66; 549/65; 549/77; 549/79; 560/124; 560/227
[58] Field of Search ............ 260/347.2, 347.4, 326 A, 260/465 D; 424/269, 274, 275, 285, 305, 304; 548/131, 132; 549/66, 79; 560/124

[56] References Cited
U.S. PATENT DOCUMENTS 4,183,948 1/1980 Huff .................... 424/304

FOREIGN PATENT DOCUMENTS 853137 2/1978 Belgium .
2802962 7/1978 Fed. Rep. of Germany .
52-14749 2/1977 Japan .

Primary Examiner—Richard Raymond
Attorney, Agent, or Firm—Sprung, Felfe, Horn, Lynch & Kramer

[57] ABSTRACT

2,2-Dimethyl-3-(2'-perfluoroalkyl-2'-perhaloalkyl-vinyl)-cyclopropane of the formula

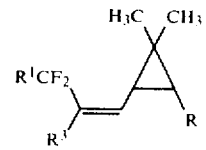

in which
R is —COOR², —COOH, —CO—Halogen, —CN or —CO—CH₃,
R¹ is fluorine or CF₃,
R³ is fluorine, chlorine, bromine or R¹CF₂—, and
R² is the radical of an alcohol which possess arthropodicidal properties. These compounds can be produced by adding a compound of the formula

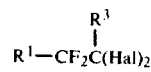

to an olefin of the formula

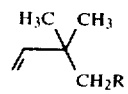

to produce a compound of the formula

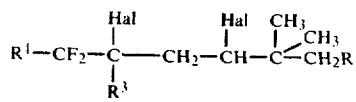

and dehydrohalogenating said compound. This compound may be hydrolyzed, saponified or esterified, depending upon the particular derivative desired.

7 Claims, No Drawings

ARTHROPODICIDAL 2,2-DIMETHYL-3-(2-PERFLUOROALKYL-2-PERHALOALKYL-VINYL)-CYCLOPROPANECARBOXYLIC ACID ESTERS

The present invention relates to and has for its objects the provision of particular new 2,2-dimethyl-3-(2'-perfluoroalkyl-2'-perhaloalkyl-vinyl)-cyclopropanecarboxylic acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

Chloroalkenyl-substituted cyclopropanecarboxylic acid esters are already known from German Offenlegungsschrift (German Published Specification) No. 2,326,077.

Alkenyl-substituted cyclopropanecarboxylic acid esters are known from German Patent Specification No. 1,926,433.

However, these compounds known from the prior art have the disadvantage of too low an activity. Their activity and their spectrum of activity are not satisfactory, especially when low concentrations are used.

1. The present invention now provides, as new compounds, the fluoroalkenyl-substituted cyclopropanecarboxylic acid esters of the general formula

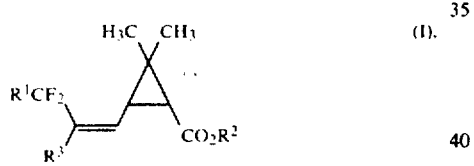

in which
R$^1$ represents fluorine or CF$_3$,
R$^3$ represents fluorine, chlorine or bromine or a radical R$^1$CF$_2$— and
R$^2$ represents the radical of an alcohol customary in the case of pyrethroids.

2. The invention also provides a process for the preparation of a fluoroalkenyl-substituted cyclopropane-carboxylic acid ester of the formula (I) in which an acid or reactive derivative thereof, of the general formula

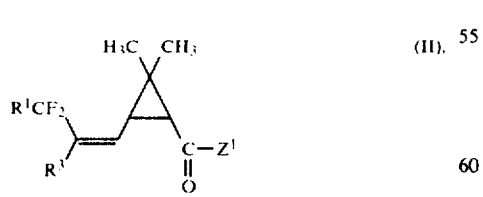

in which
R$^1$ and R$^3$ have the meanings stated under 1. (above) and
Z$^1$ denotes halogen, preferably chlorine, or OH, is reacted with an alcohol or reactive derivative thereof, of the general formula $$R^2—Z^2 \quad (III).$$

in which
R$^2$ has the meaning stated under 1. (above) and
Z$^2$ denotes OH, Cl or Br, if appropriate in the presence of a solvent and/or an acid acceptor and/or a phase-transfer catalyst.

3. The new acids and reactive derivatives thereof, of the general formula

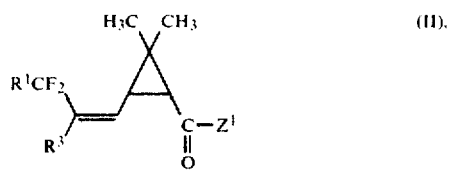

in which R$^1$, R$^3$ and Z$^1$ have the meanings stated under 2. (above) have also been found.

4. It has also been found that an acid, or reactive derivative thereof, of the formula (II), is obtained by a process in which a compound of the general formula

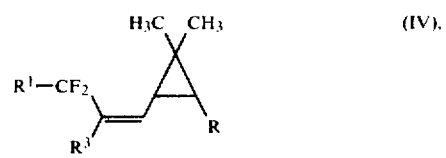

in which
R represents —COOC$_{1-4}$-alkyl, CN or —COCH$_3$ and
R$^1$ and R$^3$ have the meanings stated above, (a) is saponified in the case where R represents

alkyl or CN, or (b) is oxidized in the case where R represents

and the resulting acid, in which R denotes COOH, is optionally reacted with a halogenating agent.

5. The new compounds of the general formula

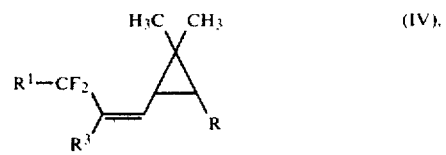

in which
R$^1$ and R$^3$ have the meanings stated under 1. (above) and
R represents ON,

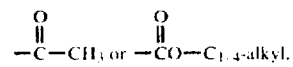

have also been found.

6. It has also been found that a compound of the formula (IV) is obtained by a process in which a compound of the general formula $$R^1-CF_2-\underset{\underset{Hal}{|}}{\overset{\overset{R^3}{|}}{C}}-CH_2-\underset{}{\overset{\overset{Hal}{|}}{CH}}-\underset{\underset{CH_3}{|}}{\overset{\overset{CH_3}{|}}{C}}-CH_2R \quad (V),$$

in which $R^1$, $R^3$ and R have the meanings stated above and

Hal represents chlorine or bromine, is dehydrohalogenated.

7. The new compounds of the general formula $$R^1CF-\underset{\underset{Hal}{|}}{\overset{\overset{R^3}{|}}{C}}-CH_2-\underset{}{\overset{\overset{Hal}{|}}{CH}}-\underset{\underset{CH_3}{|}}{\overset{\overset{CH_3}{|}}{C}}-CH_2R \quad (V),$$

in which $R^1$, $R^3$ and Hal have the meanings stated under 6. (above) and

R has the meaning stated under 5. (above), have also been found.

8. It has also been found that a compound of the formula (V) is obtained by a process in which a halogen compound of the general formula $$R^1-CF_2C(Hal)_2 \quad (VI),$$
$$\overset{\overset{R^3}{|}}{}$$

in which $R^1$ denotes fluorine or $CF_3$,

Hal denotes chlorine or bromine, the two Hal atoms being identical or different, and $R^3$ has the meaning stated under 1. (above), is added onto an olefin of the general formula $$\underset{CH_2R}{\overset{H_3C\quad CH_3}{\diagdown\diagup}}\overset{}{C} \quad (VII),$$

in which R has the meaning stated under 5. (above) if appropriate in the presence of a catalyst.

Surprisingly, the new active compounds of the formula (I) according to above exhibit a considerably higher insecticidal activity than the compounds known from the state of the art.

Preferred compounds of the formula (I) according to the invention are those in which $R^1$ represents fluorine or $CF_3$, $R^3$ denotes chlorine or bromine and $R^2$ denotes a group of the formula $$-\underset{\underset{R^{11}}{|}}{CH}-\overset{}{\underset{Y}{\diagup\diagdown}}-X-R^4, \quad \underset{\underset{R^6}{|}}{\overset{\overset{R^7}{|}}{R^7}}\overset{\overset{R^5}{|}}{\diagup\diagdown}CH_2R^6,$$
$$\overset{\overset{}{\|}}{O}$$

-continued $$\overset{N\text{———}O}{\underset{N}{\diagdown\diagup}}XR^4, \quad -CH_2-N\overset{\overset{O}{\|}}{\underset{\underset{O}{\|}}{\diagdown\diagup}}$$

$$-CH_2N\overset{\overset{O}{\|}}{\underset{\underset{O}{\|}}{\diagdown\diagup}}, \quad -\underset{\underset{R^{11}}{|}}{CH}-\overset{R^9}{\underset{R^9}{\diagup\diagdown}}\overset{R^9}{\underset{R^9}{}}$$

$$-\underset{\underset{R^{11}}{|}}{CH}-\overset{XR^{10}}{\underset{R^9}{\diagup\diagdown}} \text{ or } -CH_2-CH\overset{CH_2-\phi}{\underset{Cl}{\diagdown}}$$

wherein

Y represents O or S,

X represents $-CH_2-$, $-O-$ or $-S-$, $R^{11}$ represents hydrogen, CN, $-CO_2CH_3$, $-CO_2C_2H_5$ or $-C\equiv CH$, $R^4$ represents alkyl, alkenyl, alkynyl or an aryl or furyl group, $R^5$ represents hydrogen or methyl, $R^6$ represents an organic radical with a C—C double bond or triple bond in the α-position, $R^7$ and $R^8$ each represent hydrogen or $C_1$-$C_4$-alkyl, $R^9$ represents hydrogen, halogen or $CF_3$ and $R^{10}$ represents $-CH_2C\equiv CH$, $-CHF_2$, $-CF_3$, $-CH=CCl_2$ or an optionally substituted aryl radical (especially a phenyl radical).

Particularly preferred compounds of the formula (I) are those in which $R^2$ represents a group of the formula $$-CH_2\overset{}{\underset{O}{\diagup\diagdown}}CH_2-\phi$$

$$-CH_2\overset{}{\underset{S}{\diagup\diagdown}}CH_2-\phi$$

$$-CH_2\overset{}{\underset{S}{\diagup\diagdown}}O-\phi$$

$$-CH_2\overset{}{\underset{O}{\diagup\diagdown}}CH_2C\equiv CH.$$

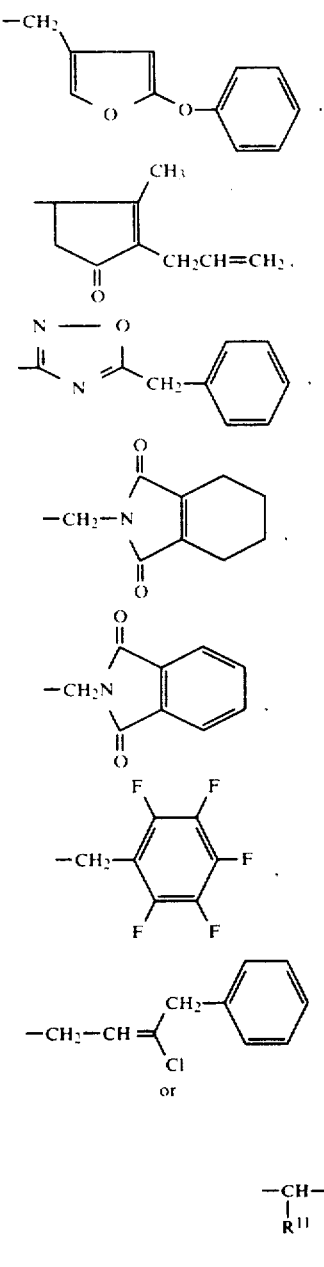

wherein

R[11] represents H, CN, —CO$_2$CH$_3$, —CO$_2$C$_2$H$_5$ or —C≡CH,

R[9] represents hydrogen or halogen and

R[10] represents —CH$_2$C≡CH, —CHF$_2$, —CF$_3$, —CH=CCl$_2$ or an aryl radical (especially phenyl) which optionally carries one or more substituents selected from halogen atoms, methyl groups and methoxy groups.

Very particularly preferred compounds of the formula (I) are those in which

R[1] represents fluorine,

R[3] denotes chlorine or bromine and

R[2] represents a group of the formula

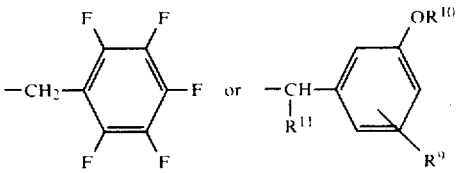

wherein

R[11] represents H or CN,

R[9] represents hydrogen or halogen (especially fluorine) and

R[10] represents an aryl radical (especially phenyl) which optionally carries one or more substituents selected from halogen atoms and methyl or methoxy groups.

The following compounds of the formula (I) may be mentioned specifically: 5'-benzyl-3'-furylmethyl-2,2-dimethyl-3-(2'-chloro-3',3',3'-trifluoro-propenyl)-cyclopropanecarboxylate, 5'-benzyl-3'-furylmethyl-2,2-dimethyl-3-(2'-bromo-3',3',3'-trifluoro-propenyl)-cyclopropanecarboxylate, 5'-benzyl-3'-furylmethyl-2,2-dimethyl-3-(2'-chloro-3',3',4',4',4'-pentafluoro-butenyl)-cyclopropanecarboxylate, 5'-phenoxy-3'-furylmethyl-2,2-dimethyl-3-(2'-chloro-3',3',3'-trifluoropropenyl)-cyclopropanecarboxylate, 3',4',5',6'-tetrahydrophthalimidomethyl-2,2-dimethyl-3-(2'-chloro-3',3',3'-trifluoro-propenyl)-cyclopropanecarboxylate, pentafluorobenzyl-2,2-dimethyl-3-(2'-chloro-3',3',3'-trifluoropropenyl)-cyclopropanecarboxylate, pentafluorobenzyl-2,2-dimethyl-3-(2'-bromo-3',3',3'-trifluoropropenyl)-cyclopropanecarboxylate, 3'-phenoxybenzyl-2,2-dimethyl-3-(2'-chloro-3',3',3'-trifluoropropenyl)-cyclopropanecarboxylate, 3'-phenoxy-α'-cyanobenzyl-2,2-dimethyl-3-(2'-chloro-3',3',3'-trifluoro-propenyl)-cyclopropanecarboxylate, 3'-phenoxybenzyl-2,2-dimethyl-3-(2'-bromo-3',3',3'-trifluoro-propenyl)-cyclopropanecarboxylate, 3'-phenoxy-α'-cyanobenzyl-2,2-dimethyl-3-(2'-bromo-3',3',3'-trifluoropropenyl)-cyclopropanecarboxylate, 3'-phenoxy-α'-cyanobenzyl-2,2-dimethyl-3-(2'-chloro-3',3',4',4',4'-pentafluoro-butenyl)-cyclopropanecarboxylate, 3'-phenoxy-α'-ethynylbenzyl-2,2-dimethyl-3-(2'-chloro-3',3',3'-trifluoro-propenyl)-cyclopropanecarboxylate, 3'-phenoxybenzyl-2,2-dimethyl-3-(2',3',3',3'-tetrafluoropropenyl)-cyclopropanecarboxylate, 3'-phenoxy-α'-cyanobenzyl-2,2-dimethyl-3-(2',3',3',3'-tetrafluoropropenyl)-cyclopropanecarboxylate, 3'-phenoxybenzyl-2,2-dimethyl-3-(2'-trifluoromethyl-3',3',3'-trifluoropropenyl)-cyclopropanecarboxylate, 3'-phenoxy-α'-cyanobenzyl-2,2-dimethyl-3-(2'-trifluoromethyl-3',3',3'-trifluoropropenyl)-cyclopropanecarboxylate, 3'-propargyloxybenzyl-2,2-dimethyl-3-(2'-chloro-3',3',3'-trifluoro-propenyl)-cyclopropanecarboxylate, 3'-dichlorovinyloxybenzyl-2,2-dimethyl-3-(2'-chloro-3',3',3'-trifluoro-propenyl)-cyclopropanecarboxylate, 3'-difluoromethoxybenzyl-2,2-dimethyl-3-(2'-chloro-3',3',3'-trifluoropropenyl)-cyclopropanecarboxylate, 3'-phenoxy-4'-fluoro-α'-cyanobenzyl-2,2-dimethyl-3-(2'chloro-3',3',3'-trifluoropropenyl)-cyclopropanecarboxylate, 3'-phenoxy-4'-fluorobenzyl-2,2-dimethyl-3-(2'-bromo-3',3',3'-trifluoropropenyl)-cyclopropanecarboxylate, 3'-(4'-fluorophenoxy)-benzyl-2,2-dimethyl-3-(2'-chloro-3',3',3'-trifluoro-propenyl)-cyclopropanecarboxylate, 3'-(4'-chlorophenoxy)-benzyl-2,2-dimethyl-3-(2'-chloro-3',3',3'-trifluoropropenyl)-cyclopropanecaboxylate and 3'-(4'-bromophenoxy)-α'-cyanobenzyl-2,2-dimethyl-3-(2'-chloro-3',3',3'-trifluoropropenyl)-cyclopropanecarboxylate.

The preparation of the fluoroalkenyl-substituted cyclopropanecarboxylic acid esters according to the invention can be represented by the equation which follows:

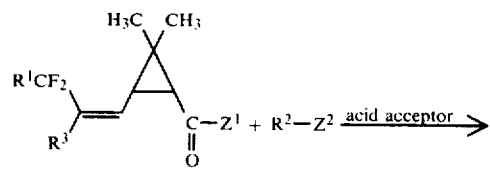

If, for example, 2,2-dimethyl-3-(2'-chloro-3',3',3'-trifluoropropenyl)-cyclopropanecarboxylic acid chloride and 3-phenoxybenzyl alcohol are used as starting materials according to process 2. (above), the course of the reaction can be represented by the equation which follows:

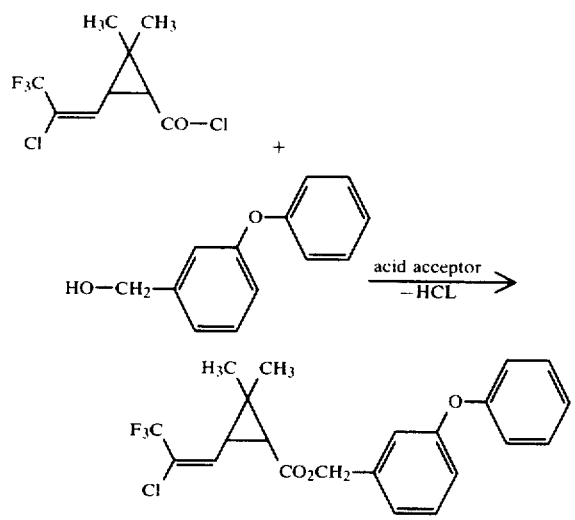

If, for example, 2,2-dimethyl-3-(2'-bromo-3',3',3'-trifluoropropenyl)-cyclopropanecarboxylic acid and 5-phenoxy-3-bromomethyl-furane are used as starting substances, the course of the reaction can be represented by the equation which follows:

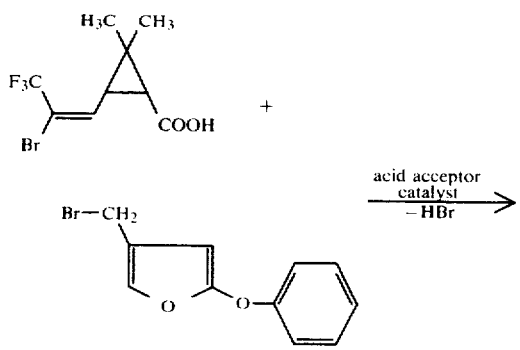

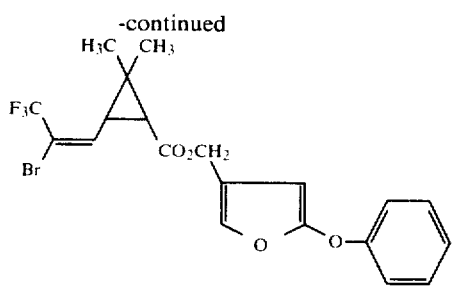

The cyclopropanecarboxylic acids and reactive derivatives thereof, of the formula (II), to be used as starting materials have not been described hitherto in the literature. The acid chlorides are preferably employed as reactive derivatives.

Specific examples which may be mentioned of the compounds of the formula (II) to be used as starting materials are: 2,2-dimethyl-3-(2'-chloro-3',3',3'-trifluoro-propenyl)-cyclopropanecarboxylic acid (and chloride), 2,2-dimethyl-3-(2'-bromo-3',3',3'-trifluoropropenyl)-cyclopropanecarboxylic acid (and chloride), 2,2-dimethyl-3-(2'-chloro-3',3',4',4',4'-pentafluorobutenyl)-cyclopropanecarboxylic acid (and chloride), 2,2-dimethyl-3-(2'-bromo-3',3',4',4',4'-pentafluorobutenyl)-cyclopropanecarboxylic acid (and chloride), 2,2-dimethyl-3-(2',3',3',3'-tetrafluoropropenyl)-cyclopropanecarboxylic acid (and chloride) and 2,2-dimethyl-3-(2'-trifluoromethyl-3',3',3'-trifluoropropenyl)-cyclopropanecarboxylic acid (and chloride).

The compounds of the formula (II) can be prepared by the process indicated under 4. (above) (see below for the details).

The alcohols and reactive derivatives, of the formula (III), likewise to be used as starting materials, are known and they can be prepared by generally customary processes described in the literature (see, for example, DT-AS (German Published Specification) or DT-OS (German Published Specification) Nos. 2,554,883, 1,926,433, 2,612,115, 2,615,435, 2,709,264, 2,436,178 and 2,436,462 and Monatshefte 67, page 35 (1936)).

Preferred compounds of the formula (III) are those in which $R^2$ has the meaning indicated above as preferred or particularly preferred.

Specific examples which may be mentioned of the compounds of the formula (III) to be used as starting materials are: 5-benzyl-3-hydroxymethyl-furane, 5-benzyl-2-hydroxymethyl-furane, 5-benzyl-3-hydroxymethyl-thiophene, 5-phenoxy-5-hydroxymethyl-furane, 3-hydroxy-4-methyl-5-allyl-cyclopent-4-en-1-one, N-hydroxymethyl-phthalimide, N-hydroxymethyl-3,4,5,6-tetrahydrophthalimide, pentafluorobenzyl alcohol, 4-phenyl-3-chloro-2-buten-1-ol, 3-trifluoromethoxybenzyl alcohol, 3-dichlorovinyloxybenzyl alcohol, 3-propargyloxybenzyl alcohol, 3-dichlorovinyloxy-α-cyano-benzyl alcohol, 3-phenoxy-benzyl alcohol, 3-phenyl-α-cyano-benzyl alcohol, 3-phenoxy-α-methoxycarbonyl-benzyl alcohol, 3-phenoxy-α-ethynyl-benzyl alcohol, 3-phenoxy-4-fluoro-benzyl alcohol, 3-phenoxy-4-chloro-benzyl alcohol, 3-phenoxy-4-fluoro-α-cyanobenzyl alcohol, 3-(4'-fluorophenoxy)-benzyl alcohol, 3-(4'-chlorophenoxy)-benzyl alcohol, 3-(4'-bromophenoxy)-benzyl alcohol, 3-difluoromethoxy-benzyl chloride, 3-phenoxy-benzyl bromide and pentafluorobenzyl chloride.

Any of the customary acid-binding agents can be used as acid acceptors for the preparation of the compounds of the formula (I) from carboxylic acids or carboxylic acid halides of the formula (II) and alcohols or chlorides or bromides of the formula (III).

Alkali metal hydroxides, carbonates and alcoholates, such as potassium hydroxide, sodium hydroxide, sodium methylate, potassium carbonate and sodium ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a substantial range. In general, the reaction of the acid halides with alcohols is carried out at about 0° to 100° C., preferably about 15° to 40° C., and the reaction of the carboxylic acids with the halides is carried out at about 50° to 150° C., preferably about 80° C. to 120° C. In the latter case, the reaction is preferably carried out in the presence of a catalyst.

Possible catalysts are all the so-called phase transfer catalysts, for example crown ethers or quaternary ammonium or phosphonium salts. Quaternary ammonium salts, for example tetrabutylammonium chloride, tetrabutylammonium bromide, benzyltriethylammonium chloride or methyltrioctylammonium chloride, are preferred.

In general, the reaction is allowed to proceed under normal pressure. The process for the preparation of the compounds (I) according to the invention is preferably carried out also using a suitable solvent or diluent. Possible solvents and diluents are virtually any of the inert organic solvents, especially aliphatic and aromatic, optionally chlorinated hydrocarbons, such as benzene, toluene, xylene, benzine, methylene chloride, chloroform, dichloroethane, chlorobenzene and o-dichlorobenzene; ethers, for example diethyl ether, diisopropyl ether or dibutyl ether; and nitriles, such as acetonitrile and propionitrile.

The starting materials are preferably employed in equimolar amounts for carrying out the process. In general, the reactants are brought together in one of the solvents indicated and, after adding the acid acceptor and if appropriate the catalyst, the mixture is stirred for one or more hours, in most cases at elevated temperature, in order to bring the reaction to completion. The reaction mixture is then poured into water and the organic phase is separated off and washed with water until netural. After drying, the solvent is distilled off in vacuo. The new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. The refractive index is used for their characterization.

The new acids and acid halides of the formula (II) can be prepared from the compounds of the formula (IV) by the process indicated under 4. (above).

In variant 4(a), in the case where R represents

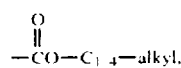

the saponification is carried out under acid or alkaline conditions in a manner which is in itself customary. Alkaline saponification is preferred.

In the case where R represents CN, the nitrile group is converted into an ester group by dissolving the nitrile in the corresponding alcohol $C_{1-4}$-alkyl-OH and saturating the solution with hydrogen chloride, usually at about 0°–20° C. After leaving the mixture to stand for some time, the imide chloride is thereby formed, from which, with water, the ester is formed.

All the customary saponifying agents can be used for the saponification, for example sulphuric acid, acetic acid or alkali metal hydroxide solutions. KOH in alcoholic solution, for example in methanol, is particularly preferred.

The saponification can be carried out at elevated temperature, for example at about 20° to 100° C., but it is preferably carried out at about 20° to 40° C.

The acids are liberated by acidifying the mixture with aqueous acids and are separated off from the salts by extraction and, if appropriate, purified by distillation.

The acid halides can be prepared by the customary methods using the customary halogenating agents, for example $SOCl_2$, $COCl_2$, $PCl_3$, $PCl_5$, oxalyl chloride, oxalyl bromide or $PBr_3$.

In variant 4(b), R represents

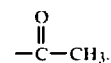

The acid is obtained by oxidation, preferably with hypochlorite (hypochlorite solution) or hypobromite. Examples of such haloform reagents are sodium hypochlorite, potassium hypochlorite, calcium hypochlorite, sodium hypobromite, potassium hypobromite and calcium hypobromite. Furthermore, the reaction can also be carried out by passing a halogen into an aqueous alkali metal hydroxide solution containing the starting compound. The reaction temperature is about −20° to +100° C., preferably about 0° to 70° C. Water is generally used as the solvent, but organic solvents can also be added as solubilizing agents. Acceleration of the reaction can be achieved by adding phase-transfer catalysts, for example quaternary ammonium salts. Possible quaternary ammonium salts are those already mentioned above.

Specific examples which may be mentioned of the new compounds of the formula (IV) are: 2,2-dimethyl-3-(2'-chloro-3',3',3'-trifluoropropenyl)-cyclopropanecarboxylic acid methyl ester, 2,2-dimethyl-3-(2'-chloro-3',3',3'-trifluoropropenyl)-cyclopropanecarboxylic acid ethyl ester, 2,2-dimethyl-3-(2'-chloro-3',3',3'-trifluoropropenyl)-cyclopropanecarboxylic acid butyl ester, 2,2-dimethyl-3-(2'-bromo-3',3',3'-trifluoropropenyl)-cyclopropanecarboxylic acid methyl ester, 1-cyano-2,2-dimethyl-3-(2'-chloro-3',3',3'-trifluoropropenyl)-cyclopropane, 1-cyano-2,2-dimethyl-3-(2'-chloro-3',3',3'-trifluoro-propenyl)-cyclopropane, 1-acetyl-2,2-dimethyl-3-(2'-chloro-3',3',3'-trifluoropropenyl)-cyclopropane and 2,2-dimethyl-3-(2'-trifluoromethyl-3',3',3'-trifluoro-propenyl)-cyclopropanecarboxylic acid ethyl ester.

The new compounds of the formula (IV) can be prepared from the compounds of the formula (V) by dehydrohalogenation by the process indicated under 6. (above). This reaction can be represented by the equation which follows:

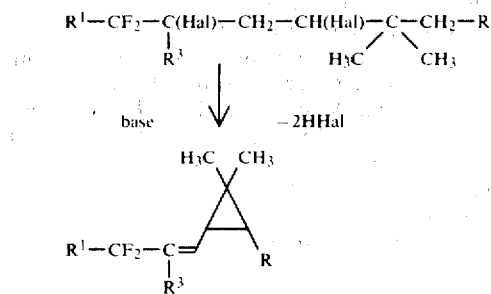

The dehydrohalogenation is effected by bases in the presence of diluents. Possible bases here are NaOH, KOH, K₂CO₃ and alcoholates, for example sodium methylate, sodium isopropylate or potassium tert.-butylate. Preferred solvents are alcohols, for example methanol, ethanol, n- or iso-propanol, butanol, tert.-butanol, glycol or glycol monomethyl ether; optionally chlorinated hydrocarbons such as benzene, toluene, xylene, chlorobenzene, dichlorobenzene or methylene chloride; and ethers, for example tetrahydrofuran, dioxane or dimethoxyethane. It is also possible to carry out the reaction in a two-phase system, for example toluene/water, especially when NaOH or KOH is used. A phase-transfer catalyst, for example a quaternary ammonium salt, can be added if appropriate. This is not only appropriate if the reaction is carried out in a two-phase system, but is also advantageous if the reaction is carried out under anhydrous conditions, for example if potassium carbonate is used as the base.

A similar reaction is described in DT-OS (German Published Specification) No. 2,539,896. However, although the preferred temperature range in that specification, when using sodium methylate or sodium ethylate, is between 60° and 100° C. (op. cit., page 31), only very little product of the formula (IV) is obtained under these conditions, and, predominantly, a further mole of hydrogen halide is split off, a product of the general formula

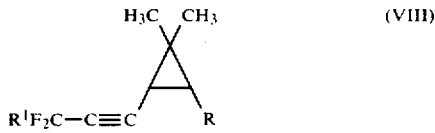

wherein R and R¹ have the meanings stated above, being formed.

Surprisingly, it has been found that virtually no product of the formula (VIII) is formed when the base, preferably NaOCH₃ or NaOC₂H₅, is initially introduced into a solvent and the compound of the formula (V) to be dehydrohalogenated is added slowly, and in particular first at about 0°–30° C. and then at about 20°–60° C., preferably about 35°–50° C., until the reaction is complete. In this case, it is particularly surprising that the dehydrohalogenation will proceed at these low temperatures.

Examples which may be mentioned of compounds of the formula (V) are: 3,3-dimethyl-4,6,6-trichloro-7,7,7-trifluoro-enanthic acid methyl ester, 3,3-dimethyl-4,6,6-trichloro-7,7,7-trifluoro-enanthic acid ethyl ester, 3,3-dimethyl-4,6,6-trichloro-7,7,7-trifluoro-enanthic acid butyl ester, 3,3-dimethyl-4,6,6-trichloro-7,7,7-trifluoro-enanthic acid nitrile, 3,3-dimethyl-4,6,6-tribromo-7,7,7-trifluoro-enanthic acid methyl ester, 2,2-dimethyl-3,5,5-trichloro-6,6,6-trifluoro-hexyl methyl ketone and 3,3-dimethyl-4,6-dichloro-6-trifluoromethyl-7,7,7-trifluoroenanthic acid ethyl ester.

The new compounds of the formula (V) are obtained from the compounds of the formula (VI) and (VII) by process 8 (above). The compounds of the formula (VI) and (VII) are known.

The process is represented by the equation which follows:

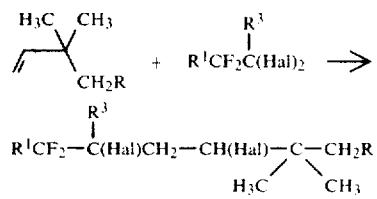

If, for example, 3,3-dimethyl-4-pentenoic acid methyl ester and 1,1,1-trichloro-2,2,2-trifluoro-ethane are used as starting materials, the course of the reaction can be represented by the equation which follows:

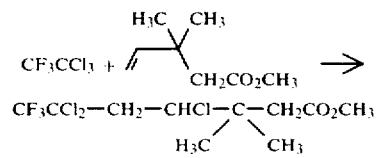

The following starting substances of the formula (VI) may be mentioned as examples: 1,1,1-trichloro-2,2,2-trifluoroethane, 1,1,1-tribromo-2,2,2-trifluoroethane, 1-chloro-1,1-dibromo-2,2,2-trifluoroethane, 1,1-dichloro-1-bromo-2,2,2-trifluoroethane, 1,1,1-trichloro-2,2,3,3,3-pentafluoropropane, 1,1,1-tribromo-2,2,3,3,3-pentafluoropropane, 1,1,1,2-tetrafluoro-2,2-dichloroethane, 1,1,1,3,3,3-hexafluoro-2,2-dichloropropane, 1,1,1,2-tetrafluoro-2,2-dibromoethane and 1,1,1,3,3,3-hexafluoro-2,2-dibromopropane.

The following starting substances of the formula (VII) may be mentioned as examples: 3,3-dimethyl-4-pentenoic acid methyl ester, 3,3-dimethyl-4-pentenoic acid ethyl ester, 3,3-dimethyl-4-pentenoic acid butyl ester, 3,3-dimethyl-4-pentenoic acid nitrile and 2,2-dimethyl-3-butenyl methyl ketone.

The process is preferably carried out under pressure, but can also be carried out under normal pressure using higher-boiling compounds of the formula (VI).

The pressure range can vary within wide limits, for example between 1 and 30 bars, preferably between 3 and 15 bars. Excess pressure can be achieved by forcing in an inert gas, for example nitrogen.

The reaction temperature can be about 50° to 200° C., but the reaction is preferably carried out at about 100° to 150° C. If appropriate, a diluent is diluent is added to the two starting substances.

Possible diluents are aliphatic or aromatic hydrocarbons, such as benzine or toluene, alcohols, such as methanol, ethanol, propanol or tert.-butanol, nitriles, such as acetonitrile or propionitrile, or dimethylformamide. Alcohols and acetonitrile are preferred.

Catalysts are required for carrying out the reaction, and in particular either (a) catalysts which supply free radicals, for example azobisisobutyronitrile, benzyl peroxide or di-tert.-butyl peroxide—the compounds of the formula (VI) being employed in equimolar amounts or, preferably, in excess—or (b) catalyst mixtures which consist of a metal salt, an amine and if appropriate a little benzoin. The metal salt can also be in the form of the hydrate and the amine can also be in the form of a salt, for example in the form of the hydrochloride.

Examples of suitable metal salts are copper(I) chloride, copper(II) chloride, iron(II) chloride, iron(III) chloride, copper(II) sulphate, cobalt chloride, zinc chloride, iron sulphate, iron acetate and copper or iron acetylacetonate.

Examples of suitable amines are dimethylamine, diethylamine, trimethylamine, triethylamine, diisopropylamine, n-butylamine, benzylamine, ethanolamine, aniline and pyridine. Dimethylamine and diethylamine (in the form of the hydrochlorides) and n-butylamine are preferred.

At least about 1.5 moles, preferably about 2–10 moles, of organic amine are preferably employed per mole of metal salt. The metal salt is employed in amounts about 0.01 to 15 mol %, preferably about 0.05 to 10 mol %, relative to the compound of the formula (VII).

It is frequently advantageous to add equimolar amounts of benzoin, relative to the metal salt.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;*
from the class of the Diplopoda, for example *Blaniulus guttulatus;*
from the class of the Chilopoda, for example *Geophilus carpophagus* and *Scutigera* spec.;
from the class of the Symphyla, for example *Scutigerella immaculata;*
from the order of the Thysanura, for example *Lepisma saccharina;*
from the order of the Collembola, for example *Onychiurus armatus;*
from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;*
from the order of the Dermaptera, for example *Forficula auricularia;*
from the order of the Isoptera, for example Reticulitermes spp.;
from the order of the Anoplura, for example *Phylloxera vastatrix, Pemphigus* spp., *Pediculus humanus corporis,* Haematopinus spp. and Linognathus spp.;
from the order of the Mallophaga, for example Trichodectes spp. and Damalinea spp.;
from the order of the Thysanoptera, for example *Hercinothrips femoralis* and *Thrips tabaci;*
from the order of the Heteroptera, for example Eurygaster spp., *Dysdercus intermedius, Piesma quadrata, Cimex lectularius, Rhodinius prolixus* and Triatoma spp.;
from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum paid,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;
from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella,* Phyllocnistis citrella, Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;*
from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;*
from the order of the Hymenoptera, for example Diprion spp., Hoplocampa spp., Lasius spp., Monomorium pharaonis and Vespa spp.;
from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;*
from the order of the Siphonaptera, for example *Xenopsylla cheopis* and Ceratophyllus spp.;
from the class of the Arachnida, for example *Scorpio maurus* and *Latrodectus mactans;*
from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating catridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synethetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titaium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that th usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The preparation of the novel compounds is shown in the following illustrative examples:

EXAMPLE 1

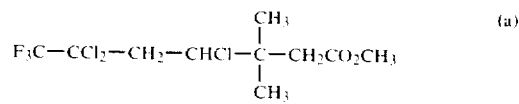

(a)

37.5 g of 3,3-dimethyl-4-pentenoic acid methyl ester, 99.4 g of 1,1,1-trichloro-2,2,2-trifluoroethane, 22 g of acetonitrile, 325 mg of $FeCl_3.6H_2O$, 255 mg of benzoin and 200 mg of dimethylamine hydrochloride were heated to 100°–120° C. in a 250 ml VA autoclave under 6 bars of nitrogen for 7 hours and the mixture was distilled over a 50 cm Vigreux column. 70 g of 3,3-dimethyl-4,6,6-trichloro-7,7,7-trifluoroenanthic acid methyl ester of boiling point: 88°-92° C./0.15 mm Hg were obtained.

The following compounds were obtained analogously:

| Intermediate | Formula | Boiling point (°C./mm) |
|---|---|---|
| (b) | F$_3$C—CCl$_2$—CH$_2$—CHCl—C(CH$_3$)(CH$_3$)—CH$_2$CO$_2$C$_2$H$_5$ | 98-102/ 0.2 |
| (c) | F$_3$C—CCl$_2$—CH$_2$—CHCl—C(CH$_3$)(CH$_3$)—CH$_2$COCH$_3$ | 82-88/ 0.2 |
| (d) | F$_3$C—CCl$_2$—CH$_2$—CHCl—C(CH$_3$)(CH$_3$)—CH$_2$CN | 104-110/ 0.25 |
| (e) | F$_3$C—CCl(CF$_3$)—CH$_3$—CHCl—C(CH$_3$)(CH$_3$)—CH$_2$CO$_2$CH$_3$ | 76-83/ 0.2 |

EXAMPLE 2

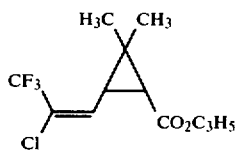
(a)

135 g of 3,3-dimethyl-4,6,6-trichloro-7,7,7-trifluoroenanthic acid methyl ester were added dropwise to a solution of 20.7 g of sodium in 300 ml of ethanol at room temperature in the course of 3 hours, while stirring. The mixture was subsequently stirred at room temperature for 1 hour and then heated to 45° C. for 7 hours. After cooling, sodium chloride which had separated out was filtered off, the filtrate was concentrated somewhat in vacuo, the residue was added to 500 ml of water and the mixture was rendered neutral. Extraction with methylene chloride and fractional distillation gave 90 g of 2,2-dimethyl-3-(2'-chloro-3',3',3'-trifluoropropenyl)-cyclopropanecarboxylic acid ethyl ester (isomer mixture) of boiling point: 55°-57° C./0.2 mm Hg.

The methyl ester was obtained with Na methylate in methanol.

EXAMPLE 3

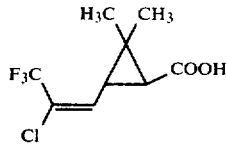

100 ml of 3 N methanolic KOH were added to 18 g of trans-2,2-dimethyl-3-(2'-chloro-3',3',3'-trifluoropropenyl)-cyclopropanecarboxylic acid ethyl ester and the mixture was stirred at room temperature for 6 hours. 300 ml of ice-water were then added and the pH was adjusted to 1 with concentrated HCl. Extraction with petroleum ether gave 11.2 g of the carboxylic acid of melting point 110°-111° C.

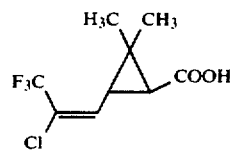

9.4 g of the cis-carboxylic acid of melting point 90°-91° C. were obtained analogously to (a) from 15 g of cis-2,2-dimethyl-3-(2'-chloro-3',3',3'-trifluoropropenyl)-cyclopropanecarboxylic acid ethyl ester.

(c) 2,2-Dimethyl-3-(2'-chloro-3',3',3'-trifluoropropenyl)-cyclopropanecarboxylic acid, which remained liquid at room temperature, was obtained analogously to (a) from 2,2-dimethyl-3-(2'-chloro-3',3',3'-trifluorophenyl)-cyclopropanecarboxylic acid ethyl ester (isomer mixture). Boiling point 90°-93° C./0.6 mm Hg.

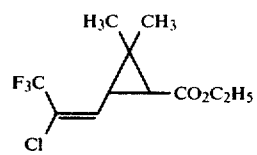

Boiling point0 103° C./16 mm Hg.
n$_D^{20}$: 1.4366 and

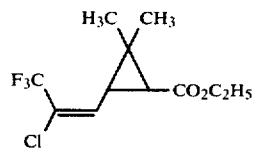

Boiling point: 102° C./16 mm Hg.
n$_D^{20}$: 1.4356 and a third isomer, probably

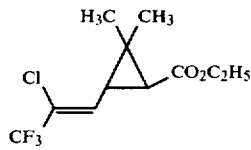

Boiling point: 105° C./16 mm Hg.
n$_D^{20}$: 1.4364
were isolated in the pure form, by distillation on an annular gap column, from the isomer mixture which was obtained in the preparation of 2,2-dimethyl-3-(2'-chloro-3',3',3'-trifluoromethyl)-cyclopropanecarboxylic acid ethyl ester.

Preparation of starting materials and their precursors

EXAMPLE 4

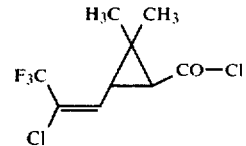

20 g of trans-2,2-dimethyl-3-(2'-chloro-3',3',3'-trifluoropropenyl)-cyclopropanecarboxylic acid were dissolved in 150 ml of methylene chloride, a few drops of dimethylformamide were added and phosgene was passed in at room temperature until the reaction had ended (monitoring by the infrared spectrum). Excess phosgene and methylene chloride were then distilled off. The residue distilled at 40°–50° C./0.5 mm Hg. The refractive index of trans-2,2-dimethyl-3-(2'-chloro-3',3',3'-trifluoropropenyl)-cyclopropanecarboxylic acid chloride was $n_D^{20}$: 1.4554.

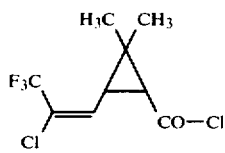

(b)

10 g of cis-2,2-dimethyl-3-(2'-chloro-3',3',3'-trifluoropropenyl)-cyclopropanecarboxylic acid were dissolved in 50 ml of thionyl chloride and the solution was heated to the boil for one hour. After distilling off the excess thionyl chloride, the residue was distilled under a high vacuum. Cis-2,2-dimethyl-3-(2'-chloro-3',3',3'-trifluoropropenyl)-cyclopropanecarboxylic acid chloride of boiling point 52°–54° C./0.9 mm Hg and $n_D^{20}$: 1.4520 was obtained.

(c) 2,2-Dimethyl-3-(2'-chloro-3',3',3'-trifluoropropenyl)-cyclopropanecarboxylic acid chloride was obtained from 2,2-dimethyl-3-(2'-chloro-3',3',3'-trifluoropropenyl)-cyclopropanecarboxylic acid in the same manner as in (a) or (b), a stereoisomer mixture which contained all 4 possible stereoisomers having been employed.

EXAMPLE 5

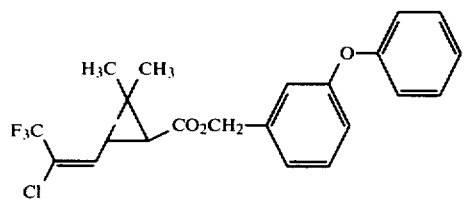

(1)

5 g of trans-2,2-dimethyl-3-(2'-chloro-3',3',3'-trifluoropropenyl)-cyclopropanecarboxylic acid chloride were mixed with 100 ml of toluene and 3.85 g of 3-phenoxybenzyl alcohol. 1.5 g of pyridine in 50 ml of toluene were then added dropwise at room temperature, while stirring, and the mixture was subsequently stirred at room temperature for 4 hours. 150 ml of water were then added to the reaction mixture and the organic phase was separated off and washed with 100 ml of water. The organic phase was dried with sodium sulphate and filtered, the filtrate was concentrated on a rotary evaporator and the residue was subjected to incipient distillation at 60° C. under a high vacuum (for about 1 hour).

The residue weighed 6.1 g and consisted of trans-2,2-dimethyl-3-(2'-chloro-3',3',3'-trifluoropropenyl)-cyclopropanecarboxylic acid (3'-phenoxy)-benzyl ester; $n_D^{20} = 1.5292$.

EXAMPLE 6

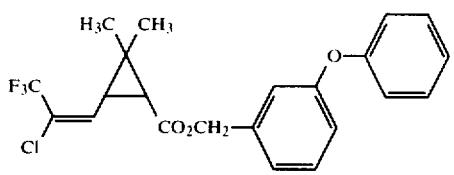

(2)

3.2 g of cis-2,2-dimethyl-3-(2'-chloro-3',3',3'-trifluoropropenyl)-cyclopropanecarboxylic acid (3'-phenoxy)benzyl ester were obtained analogously to Example 5 from 3.2 g of cis-2,2-dimethyl-3-(2'-chloro-3',3',3'-trifluoropropenyl)-cyclopropanecarboxylic acid chloride, 2.44 g of 3-phenoxybenzyl alcohol and 0.97 g of pyridine. $n_D^{20} = 1.5295$.

EXAMPLE 7

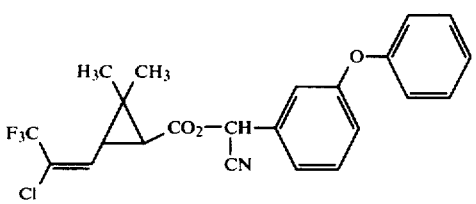

(3)

5 g of trans-2,2-dimethyl-3-(2'-chloro-3',3',3'-trifluoropropenyl)-cyclopropanecarboxylic acid chloride were mixed with 100 ml of toluene and 4.28 g of the cyanohydrin of 3-phenoxybenzaldehyde. 1.5 g of pyridine in 50 ml of toluene were then added dropwise at room temperature, while stirring, and the mixture was subsequently stirred at room temperature for 4 hours. 150 ml of water were then added to the reaction mixture and the organic phase was separated off and washed with 100 ml of water. The organic phase was dried with sodium sulphate and filtered, the filtrate was concentrated on a rotary evaporator and the residue was subjected to incipient distillation at 60° C. under a high vacuum (for about 1 hour). The residue weighed 7.2 g and consisted of trans-2,2-dimethyl-3-(2'-chloro-3',3',3'-trifluoropropenyl)-cyclopropanecarboxylic acid (3'-phenoxy)-α-cyanobenzyl ester; $n_D^{20} = 1.5281$.

EXAMPLE 8

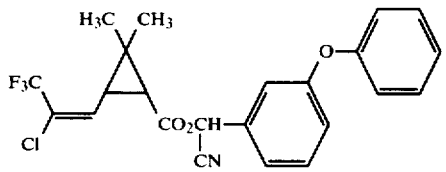

(4)

4.4 g of cis-2,2-dimethyl-3-(2'-chloro-3',3',3'-trifluoropropenyl)-cyclopropanecarboxylic acid (3'-phenoxy)-α-cyanobenzyl ester were obtained analogously to Example 7 from 3.2 g of cis-2,2-dimethyl-3-(2'-chloro-3',3',3'-trifluoropropenyl)-cyclopropanecarboxylic acid chloride, 2.75 g of the cyanohydrin of 3-phenoxybenzaldehyde and 0.97 g of pyridine. $n_D^{20} = 1.5271$.

The following compounds were prepared analogously to Examples 5-8, isomer mixtures of the acid chloride being used as starting substances:

| Compound No. | Formula |
|---|---|
| 5 | (F₃C)(Cl)C=CH—[cyclopropane(H₃C,CH₃)]—CO₂CH₂—C₆H₄—OCHF₂ |
| 6 | (F₃C)(Cl)C=CH—[cyclopropane(H₃C,CH₃)]—CO₂CH₂—C₆H₄—OCF₃ |
| 7 | (F₃C)(Cl)C=CH—[cyclopropane(H₃C,CH₃)]—CO₂CH₂—C₆F₅ |
| 8 | (F₃C)(Cl)C=CH—[cyclopropane(H₃C,CH₃)]—CO₂CH₂—C₆H₄—O—C₆H₄—F |
| 9 | (F₃C)(Cl)C=CH—[cyclopropane(H₃C,CH₃)]—CO₂CH₂—C₆H₄—OCH=CCl₂ |
| 10 | (F₃C)(Cl)C=CH—[cyclopropane(H₃C,CH₃)]—CO₂CH₂—C₆H₄—OCH₂C≡CH |
| 11 | (F₃C)(Cl)C=CH—[cyclopropane(H₃C,CH₃)]—CO₂CH(CN)—C₆H₃(F)—O—C₆H₅ |
| 12 | (F₃C)(Cl)C=CH—[cyclopropane(H₃C,CH₃)]—CO₂—CH(CN)—C₆H₄—O—C₆H₄—F |

The insecticidal and acaricidal activity of the compounds of this invention is illustrated by the following examples wherein the compound according to the present invention are each identified by the number (given in brackets) from preparative Examples 5-8 hereinabove:

EXAMPLE 9

Phaedon larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound of the desired concentration and were infested with mustard bettle larvae (*Phaedon cochleariae*), as long as the leaves were still wet.

After the specified periods of time, the degree of destruction was determined in %: 100% meant that all of the beetle larvae had been killed whereas 0% meant that none of the beetle larvae had been killed.

In this test, for example, the following compounds showed a superior activity compared to the prior art: (2) and (4).

EXAMPLE 10

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (2) and (4).

EXAMPLE 11

Test insect: *Phorbia antiqua* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil. The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compound showed a superior action compared to the prior art: (1) and (3).

EXAMPLE 12

Test insects: *Blatta orientalis*
Number of test insects: 10
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% denoted that all of the test insects had been killed; 0% denoted that none of the test insects had been killed.

In this test, for example, the following compounds showed a superior action compared to the prior art: (1), (2) and (4).

EXAMPLE 13

LT$_{100}$ test for *Diptera*

Test insects: *Aedes aegypti*
Number of test insects: 25
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. The stated number of test insects was then placed in the Petri dish and the dish was covered with a glass lid.

The condition of the test insects was continuously observed. The time which was necessary for 100% "knockdown" was determined.

In this test, for example, the following compounds showed a superior action compared to the prior art: (1), (2), (3) and (4).

It will be appreciated that the instant specification and examples are set forth by way of illustration and not limitation, and that various modifications and changes may be made without departing from the spirit and scope of the present invention.

What we claim is:

1. A 2,2-dimethyl-3-(2'-perfluoroalkyl-2'-perhaloalkyl-vinyl)-cyclopropane derivative of the formula

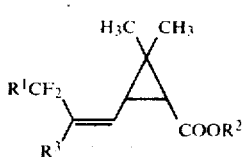

in which
R$^1$ is fluorine or CF$_3$,
R$^3$ is fluorine, chlorine, bromine or R$^1$CF$_2$-, and
R$^2$ is pentafluorobenzyl, a fluorine-substituted 3-phenoxybenzyl or fluorine-substituted α-cyano-3-phenoxybenzyl.

2. A compound according to claim 1, in which R$^1$ is fluorine, R$^3$ is chlorine, and R$^2$ is pentafluorobenzyl or fluorine-substituted α-cyano-3-phenoxybenzyl.

3. A compound according to claim 1, in which said compound is 2,2-dimethyl-3-(2'-chloro-3',3',3'-trifluoropropenyl)-cyclopropanecarboxylic acid pentafluorobenzyl ester of the formula

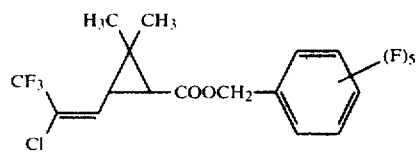

4. A compound according to claim 1, in which said compound is 2,2-dimethyl-3-(2'-chloro-3',3',3'-trifluoropropenyl)-cyclopropanecarboxylic acid α-cyano-4-fluoro-3-phenoxy-benzyl ester

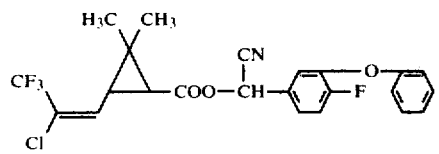

5. An arthropodicidal composition containing as active ingredient an arthropodicidally effective amount of a compound according to claim 1 in admixture with a diluent.

6. A method of combating arthropods which comprises applying to the arthropods, or to a habitat thereof, an arthropodicidally effective amount of a compound according to claim 1.

7. The method according to claim 6, in which said compound is 2,2-dimethyl-3-(2'-chloro-3',3',3'-trifluoropropenyl)-cyclopropanecarboxylic acid (3'-phenoxy)-α-cyanobenzyl ester, 2,2-dimethyl-3-(2'-chloro-3',3',3'-trifluoropropenyl)-cyclopropanecarboxylic acid pentafluorobenzyl ester, or 2,2-dimethyl-3-(2'-chloro-3',3',3'-trifluoropropenyl)-cyclopropanecarboxylic acid α-cyano-4-fluoro-3-phenoxy-benzyl ester, and it is applied to a domesticated animal to free it of parasitical insects and acarids.

* * * * *